United States Patent [19]

Weisbart

[11] Patent Number: 5,252,461

[45] Date of Patent: * Oct. 12, 1993

[54] MIXED IMMUNOGLOBULINS FOR DETECTION OF RHEUMATOID FACTORS

[75] Inventor: Richard Weisbart, Los Angeles, Calif.

[73] Assignee: The Regents of the Univ. of California, Oakland, Calif.

[*] Notice: The portion of the term of this patent subsequent to Aug. 24, 2010 has been disclaimed.

[21] Appl. No.: 826,894

[22] Filed: Jan. 28, 1992

Related U.S. Application Data

[63] Continuation-in-part of Ser. No. 772,434, Oct. 7, 1991, Pat. No. 5,238,851, which is a continuation-in-part of Ser. No. 517,246, May 1, 1990, abandoned.

[51] Int. Cl.$^5$ .................. C12Q 1/00; G01N 33/53; G01N 33/566
[52] U.S. Cl. .................. 435/7.92; 435/7.1; 435/7.93; 435/7.94; 435/7.95; 436/501; 436/503; 436/506; 436/572; 436/509; 436/513; 436/518; 436/536
[58] Field of Search .................. 435/7.1, 7.92, 7.93, 435/7.94, 7.95; 436/509, 501, 503, 506, 512, 513, 518, 536

[56] References Cited

U.S. PATENT DOCUMENTS 4,012,494  3/1977  Ling .
4,197,361  4/1980  Hoff et al. .
4,299,916  11/1981  Litman et al. .
4,486,530  12/1985  David et al. .
4,540,659  9/1985  Litman et al. .
4,753,893  6/1988  Roper .

OTHER PUBLICATIONS

Pope et al (1981) J Clin Med 97:842-853.
Clark (1980) "The Experimental Foundations of Modern Immunology" John Wiley & Sons, N.Y. pp. 28-47.
M. Wilchek, et al., *Immunology Today*, vol. 5, No. 2, pp. 39-43 (1984).
J. T. Barrett, *Textbook of Immunology*, 3d Ed., C. V. Mosby Company, St. Louis, Mo., pp. 428-430 (1978).

*Primary Examiner*—Christine M. Nucker
*Assistant Examiner*—David R. Preston
*Attorney, Agent, or Firm*—Poms, Smith, Lande & Rose

[57] ABSTRACT

Assays are provided for detecting the existence of active rheumatoid arthritis by detecting rheumatoid factor as a blood component which cross-links human IgG with sheep IgG. Particularly, an enzyme labelled assay is provided using biotin-avidin to link the enzyme to the immunoglobulin. The binding peptide of the rheumatoid factor is also provided.

9 Claims, No Drawings

MIXED IMMUNOGLOBULINS FOR DETECTION OF RHEUMATOID FACTORS

CROSS-REFERENCE TO RELATED APPLICATIONS

This application is a continuation-in-part of application Ser. No. 07/772,434, now U.S. Pat. No. 5,238,851 filed Oct. 7, 1991, which is a continuation-in-part of application Ser. No. 07/517,246, filed May 1, 1990, now abandoned.

INTRODUCTION

1. Technical Field

The field of the subject invention is the detection of rheumatoid factor.

2. Background

Rheumatoid factors are antiglobulin antibodies that bind heterogeneous determinants on the crystallizable fragment (Fc) of IgG immunoglobulins and are found in the serum and synovial fluid of most patients with rheumatoid arthritis. The role of rheumatoid factors in the pathogenesis of rheumatoid arthritis has been questioned because they are also present in patients with various other chronic diseases, suggesting that their presence is non-specific. However, the binding specificity of rheumatoid factors is diverse and includes allotypic antigens (Gm) on human IgG, neoantigens created within IgG by the formation of the immune complexes, and cross-reactive antigens shared by other mammalian IgG immunoglobulins.

Rheumatoid factors that bind alloantigens may occur as a result of blood transfusions and pregnancy, but they do not represent true autoantibodies unless they bind self determinants. Rheumatoid factors that bind neoantigens are also not true autoantibodies, as they are directed to new determinants formed within immune complexes. In contrast, the presence of an autologous reactive rheumatoid factor specificity, Ga, in rheumatoid serum has been demonstrated.

The presence of autoreactive rheumatoid factors in circulating immune complexes from patients with rheumatoid arthritis supports a potential pathogenic role for these autoantibodies. However, the method currently used to detect rheumatoid factors does not exclusively identify the presence of autoreactive antibodies. Moreover, techniques to measure disease related rheumatoid factor autoantibodies are too complex to permit an evaluation of their specificity for rheumatoid arthritis. It is therefore of great interest to be able to develop techniques which have significant specificity for rheumatoid arthritis.

3. Relevant Literature

A monoclonal antibody hRF-1 isolated from synovial tissue of a patient with rheumatoid-like arthritis that binds multiple mammalian IgG immunoqlobulins has been described by Weisbart et al., J. Immunol. 1987; 139 2925-2928. The presence of an autologous reactive rheumatoid factor specificity, Ga in rheumatoid serum has been reported by Allen and Kunkel, Arth Rheumatism 1966; 9:758-768. General descriptions of rheumatoid factors may be found in Waller, Acta Pathol Microbiol Scand 1940; 17:172-188; Rose et al., Proc Soc Exp Biol Med 1948; 68:1-6 and Natvig et al., Clin Exp Immunol 1972; 12:177-183. Cohen et al., J Immunology 1987; 139:I466 report that IgG RF show a predominance of IgG antibodies in RA patients. Carsen, Rheumatoid Factor In: Textbook of Rheumatology (Kelly et al., eds.) W. B. Saunders Co., Philadelphia, Pa. 1981, p. 685; and Pope and McDuffy, J Lab Clin Med 1981; 97:842-853 discuss the binding of RF in RA serum to heterologous mammalian IgG. The latter reference also reports that horse IgG provides a more sensitive assay for detecting RF in rheumatoid arthritis patient's sera. Butler and Vaughan describe the reaction of rheumatoid factor with animal gamma globulins, Immunology 1965; 8:144-159.

SUMMARY OF THE INVENTION

Rheumatoid factor is assayed in a sandwich assay, employing as ligands for the rheumatoid factor, human IgG and sheep IgG. Particularly, an ELISA assay is employed for detection of rheumatoid factor, particularly associated with patients with rheumatoid arthritis who have active disease.

DESCRIPTION OF THE SPECIFIC EMBODIMENT

An improved sensitive assay is provided for the detection of rheumatoid factor in human patients, particularly having an active form of the disease. The method provides detection of the presence of a component in human serum which provides a crosslink between human IgG and ovine IgG, particularly sheep IgG. By providing for one of the IgG ligands to be bound to a solid support and the other free in solution, particularly the sheep IgG bound to the support, a sensitive assay is achieved. Particularly, the assay has a low incidence of providing false positives, while providing for a high correlation between the active form of rheumatoid arthritis and a positive result.

The ovine IgG may be obtained from any convenient source and is available commercially. Conventional techniques for isolating IgG from mammalian blood are amply described in the literature. Ovine IgG may be obtained, for example, from Organon Teknika, West Chester, Pa.. The human IgG may be obtained by any convenient means, either from commercial sources or by employing conventional techniques for IgG isolation. The IgG may be obtained from any conventional bulk source, where the blood is derived from numerous individuals and pooled to have an average composition. (By "pooled" it is intended that the Ig has come from a plurality of individuals of the same species which individuals were not immunized against any particular known antigen.) Thus, abattoirs, blood banks, etc. may be original sources. Thus, the IgGs do not have a significant level of an IgG against one or a few antigens. To the extent that the IgG is pooled, the composition has no particular specificity so that the primary characteristic of the composition is the IgG Fc isotypes.

The sera which are employed as the sample will usually be diluted at least 1:20, more usually at least about 1:80, and may be diluted at least about 1:100. Desirably, the cutoff for a positive result will be at a dilution of at least about 1:100, or at least about 1:150.

The non-bound ligand IgG will be labelled, either directly or indirectly, with a label providing for a detectable signal. A wide variety of labels are known, such as enzymes, radioisotopes, fluorescers, chemiluminescers, particles, etc. These labels may be covalently conjugated to the IgG ligand or to another molecule which will bind to the IgG ligand. For example, the non-bound IgG may be conjugated with a small molecule such as biotin and the detectable label bonded to streptavidin or avidin (hereafter called "avidin"). By carrying out a two step assay, where the sample is combined with the two different IgG ligands, the labeled avidin may then be added to determine the presence of specifically bound human or ovine IgG ligand to the support.

The assay may be carried out in any convenient form as a sandwich assay. That is, the bound IgG ligand may be covalently or non-covalently bound to a surface, which may be the wall of a container, e.g. a microtiter plate well, beads, e.g. controlled pore glass beads, Pyrex beads, etc., capillary tube walls, or the like. Methods for binding proteins to a surface are well known and need not be described here. The surface may be an active surface, where covalent reactions occur between a functional group on the surface and the protein or a surface where the protein binds non-specifically, particularly after heating, and is retained during the course of the assay. Various activated substrates are available having functional groups which will bind to the protein. Functional groups include activated carboxyl groups, imino groups, aldehydes, etc.

Specific labels of interest include enzymes, such as hydrolases and oxidoreductases, such as alkaline phosphatase, beta-galactosidase, glyceryl-3-phosphate dehydrogenase, malate dehydrogenase, glucose-6-phosphate dehydrogenase, horseradish peroxidase, glucose oxidase, uricase, xanthine oxidase, etc. Fluorescers which may be employed include phycobiliproteins, fluorescein, dansyl, rhodamine, umbelliferone, etc.

In carrying out the assay, the sample is contacted with the substrate bound IgG ligand. The blood sample may have been subjected to prior treatment, such as removal of red blood cells to provide for serum or plasma, citration, particularly dilution with buffer, or the like. Usually, the sera will be diluted in order to provide for an appropriate cutoff to insure the substantial absence of false positives.

Various buffers may be employed, being selected to be compatible with the assay. Buffering agents include Tris, MOPS, HEPES, phosphate, borate, carbonate, etc. The particular buffer will be primarily a matter of arbitrary choice, although one buffer may be preferred as compared to another in a particular assay protocol associated with a particular label. Generally, the buffer concentration will range from about 10 to 400 mM and the pH will generally range from about 5 to 11, more usually from about 6 to 10. Other components may include inert proteins, such as bovine serum albumin or ovalbumin, to reduce non-specific binding, the added proteins usually being present in not more than about 2%.

The particular order of addition of the sample and the non-bound IgG ligand is not critical, although preferably the sample and labeled IgG ligand are added simultaneously to the bound IgG ligand. The assay mixture may then be incubated for at least 30 minutes, preferably at least one hour, more preferably at least about six hours, and then determined as appropriate, depending upon whether the labelled IgG ligand has a detectable label or requires binding of a detectable label. Substantial excess of the labelled ligand may be employed to ensure optimum binding up to saturation of available sites of RF in the sera.

After the incubation, the supernatant is removed, the surface washed thoroughly with buffered solution, e.g. the buffer employed to dilute the sample, and as appropriate, the presence of specifically bound label detected.

Where the label is bound to the IgG ligand, labels which can be read directly, e.g. radioisotopes or fluorescers, may be measured. Where a detectable labelled entity is required, such as labelled avidin, the labelled entity is added to ensure complete binding to any of the complementary specific binding member present on the surface. As appropriate, the label may be directly determined or with an enzyme, substrate added and the presence of a detectable molecule measured. For the most part, enzyme substrates will involve leuco dyes which result in colored dyes or fluorescers.

The subject methodology can be readily automated, where additions, incubations and the like, can be controlled, washings provided, and results read.

The subject reagents may be conveniently provided as a kit, where the surface bound IgG ligand, the labelled ligand, either by itself or in conjunction with a labelled specific binding molecule are provided in appropriate amounts to be used in the subject assay. Conveniently, for an enzyme label, substrate may also be included, with other reagents, such as buffer, inert protein, e.g. ovalbumin and the like.

The human rheumatoid factor identified by the subject assay may be subjected to protease degradation to provide fragments of at least about 8 amino acids, preferably at least about 12 amino acids. Usually the fragment will be fewer than about 60 amino acids, more usually fewer than about 30 amino acids. Various proteases may be used individually or in combination Proteases which may find use are trypsin, chymotrypsin, pepsin, papain, chymopapain, or other endopeptidases. The fragments may be separated by chromatography, e.g. reverse phase high performance liquid chromatography, electrophoresis, or other separation technique which separates by polarity and/or size. The fragments are then screened for binding to both human and ovine IgG and competing with human rheumatoid factor in the subject assay. The fragments may be sequenced and the sequences synthesized in accordance with known techniques.

The binding fragments may be used in competitive assays. The fragments will inhibit the amount of dispersed IgG which can bind to the support through the binding to rheumatoid factor bound to the support. By having a detectable label on the fragment, the amount of the fragment bound to the support will be proportional to the amount of rheumatoid factor present in the sample. One also labels the dispersed IgG with a different label and measures both labels, so that one has a confirmation of the result where one detects both the amount of sample immunoglobulin which binds solely to the bound Ig and the amount of sample immunoglobulin which binds to the ovine and human IgG's.

Various combinations of labels may be used, such as fluorescers which have substantially different absorption and emission ranges, enzymes which provide products which can be detected independently, and the like. Alternatively, biotin or other ligand may be used, which may then be detected by adding a labeled specific binding member, which binds to the ligand.

The fragment may be readily labeled in accordance with conventional ways. By employing available carboxyl or amino groups, functionalized fluorescers may be covalently bound to the peptide. Cross-linking agents may be used with enzymes. Normally, there will be only a few, usually from 1 to 2, labels present on the fragment. The labeling will be selected so as to not interfere with the binding of the fragment to the IgG's.

Desirably, the fragment will be synthesized, so that the label may be part of the synthesis.

The fragments may also find other uses, e.g. therapeutic uses for preventing aggregation of rheumatoid factor with immunoglobulins in vivo. By administering the fragments to a patient during an inflammatory episode, binding of the rheumatoid factor with IgG will be inhibited. The fragments may be stabilized by being modified with polyethylene glycol, by being joined to a stable protein sequence, by being incorporated into a liposome lumen, and the like. The fragments or modified form thereof may be administered parenterally in a physiologically acceptable medium, e.g. saline, PBS, aqueous ethanol, etc., in an amount to reduce aggregation of IgG by rheumatoid factor in the host The following examples are offered by way of illustration and not by way of limitation.

EXPERIMENTAL

Rheumatoid Factor Assays 96 well microtiter plates were coated with purified sheep IgG. IgG (10 µg/ml) in 0.06M carbonate buffer, pH 9.6 was incubated overnight at 4° C. in 96-well plates. Sera were assayed at a dilution of 1:160 and IgG rheumatoid factor was detected employing human IgG biotinylated using NHS-LC-BIOTIN (Pierce, Rockford, Ill.). Included in the incubating solution was 0.625 µg of biotinylated human IgG. After the incubation, excess horseradish peroxidase conjugated streptavidin was added (0.1 µg/ml in 100 µl), the plates washed with PBST, and the conversion of 2,2' azino-di-1,3-ethylbenzthiazolinsulfonate to a chromophore with an optical density (absorbance) maximum at 414 nm monitored. A negative control was included in each assay by measuring binding to a plate coated with ovalbumin alone. A known positive serum from a patient with rheumatoid arthritis was used as a positive control in each assay and the results were expressed as percent of the positive control.

Sera from 704 subjects were assayed for rheumatoid factors with autologous binding and/or simultaneous binding to human IgG and sheep IgG. The human serum was added, diluted 1:100 with ovalbumin in PBS or phosphate buffered saline.

SUBJECTS AND METHODS

Subjects

Serum was obtained from 704 patients, including 108 with classical rheumatoid arthritis (Group 1) defined by revised criteria of the American Rheumatism Association (Arnett et al. Arth. Rheumatism 1988; 31:315-324. 231 patients were studied with connective tissue diseases other than rheumatoid arthritis (Group 2), including 190 with systemic lupus erythematosus, 31 with progressive systemic sclerosis, 3 with polymyositis, 4 with temporal arteritis, and 3 with polyarteritis nodosa. Also studied were sera from 317 hospitalized patients with non-rheumatic diseases (Group 3) in addition to sera from 48 healthy individuals. Sera was stored at −20° C. until assayed.

A prospective study was done to evaluate the relationship between rheumatoid factors and rheumatoid arthritis disease activity. Rheumatoid arthritis disease activity was evaluated by physicians in 40 patients at the time serum was obtained. An index of disease activity was based on the number of swollen or tender joints, the patient's subjective evaluation of pain, and a quantitative estimate of the duration of morning stiffness. Each parameter was given a value from zero (inactive) to five (most active), and the activity index was recorded as the sum of the three values. A Westergren erythrocyte sedimentation rate was obtained in 23 of these patients as an additional objective measure of disease activity.

RHEUMATOID FACTORS MEASURED BY THE AGGLUTINATION OF LATEX PARTICLES

All sera were assayed for rheumatoid factors by the agglutination of latex beads coated with heat aggregated human IgG (RF Test, Difco, Detroit, Mich.). Sera were assayed in 2-fold serial dilutions beginning with 1:20, and positive tests were selected as those with a titer of 1:160 or greater. By choosing a titer of 1:160, low titer responses were eliminated that occurred more frequently in non-rheumatoid arthritis patients. Moreover, at titers of 1:160 or greater, the positive rheumatoid factor tests in non-rheumatoid arthritis patients were comparable to those found in patients with rheumatoid arthritis.

RHEUMATOID FACTORS MEASURED BY ELISA

Sera that agglutinated latex particles also were assayed by ELISA using 96-well mirotiter plates coated overnight at 4° C. with 10 µg/ml purified native human IgG (Assay A), human IgG aggregated by heating to 63° C. for 30 minutes, and purified mammalian IgG immunoglobulins, including, sheep, horse, rabbit, mouse, guinea pig, and goat IgG (Assay B). The plates were washed three times with phosphate buffered saline containing 0.05% Tween-20 (PBST), and human serum (0.1 mL) diluted 1:100 with 1% ovalbumin was incubated in the wells overnight at 4° C. The plates were washed with PBST, and affinity purified, alkaline phosphatase conjugated goat antibodies specific for human IgM Fc were added for one hour at room temperature. Preliminary tests showed that the conjugated antiserum used did not competitively inhibit the rheumatoid factor assay. After the wells were washed with PBST, alkaline phosphatase was measured by absorbency by the conversion of p-nitrophenylphosphate to p-nitrophenol at 405 nm.

STATISTICAL ANALYSIS

The precision of the double-binding test for rheumatoid factor was evaluated by intra-batch and interbatch comparisons and expressed as the coefficient of variation, V, where V=standard deviation ($\sigma$)/mean ($\mu$).

RESULTS

RHEUMATOID FACTORS MEASURED BY THE AGGLUTINATION OF LATEX PARTICLES

Sera were assayed in 2-fold serial dilutions beginning at 1:20. In order to compare sera with comparable levels of rheumatoid factor in patients with and without rheumatoid arthritis, a serum dilution of 1:160 was selected for inclusion as a positive test. At a dilution of 1:160, serum from 41/108 (38.0%) patients with rheumatoid arthritis agglutinated IgG-coated latex particles. In contrast, 14/231 (6.1%) patients with other connective tissue diseases, primarily systemic lupus erythematosus, and 19/317 (6.0%) patients with non-rheumatic diseases had positive rheumatoid factor tests (total positive tests=33/548, or 6.0%). The median titer of positive responses in both rheumatoid and non-rheumatoid arthritis patients was 1:320. The latex agglutination test was, therefore, 38.0% sensitive and 94.0% specific for rheumatoid arthritis when sera were assayed at dilutions of 1:160 or greater.

The data presented above is summarized below in Table 1.

TABLE 1

| PATIENT GROUP NUMBER | NUMBER OF PATIENTS TESTED | ASSAY RESULTS (%) |
|---|---|---|
| 1 (RA patient) | 108 | 38 - sensitivity |
| 2 (connective tissue patient) | 231 | 93.9 - specificity |
| 3 (non-connective tissue patient) | 317 | 94.0 - specificity |

RHEUMATOID FACTORS MEASURED BY ELISA THAT CROSS-LINK HUMAN IgG AND SHEEP IgG

Rheumatoid factors that cross-link human IgG and sheep IgG were assayed in serum from 704 subjects. Positive tests were defined as binding greater than 28% of a standard positive control, since 28% corresponded to 2 S.D. above the mean response for the control group of 548 patients without rheumatoid arthritis. The results of the cross-linking assay showed that it was comparable in sensitivity (39/108, 36.1%) to the latex agglutination test (41/108, 38.0%). In contrast to the latex agglutination test, the cross-linking of human IgG and sheep IgG was considerably more specific, since positive tests occurred in only 2/317 (0.6%) of patients with non-rheumatic diseases, in only 3/231 (1.3%) patients with rheumatic diseases other than rheumatoid arthritis, and in 0/48 healthy individuals. The total number of positive tests in subjects without rheumatoid arthritis was 5/596, or only 0.8% This ELISA for rheumatoid factors that cross-link human IgG and sheep IgG was, therefore, 99.2% specific for rheumatoid arthritis compared to only 94.0% for the latex agglutination test ($\chi^2=24.2$, $p<0.001$). Based on a prevalence rate of 1.0% for rheumatoid arthritis, the positive predictive value for the latex agglutination test for serum diluted 1:160 is 6.0% compared to 31.3% for rheumatoid factors that cross-link human IgG and sheep IgG. The cross-linking assay was not positive in any of the non-rheumatoid arthritis patients with latex agglutination titers less than 1:160.

The data presented above is summarized below in Table 2.

TABLE 2

| PATIENT GROUP NUMBER | NUMBER OF PATIENTS TESTED | ASSAY RESULTS (%) |
|---|---|---|
| 1 (RA patient) | 108 | 36.1 - sensitivity |
| 2 (connective tissue patient) | 231 | 98.7 - specificity |
| 3 (non-connective tissue patient) | 317 | 94.4 - specificity |

RHEUMATOID FACTORS IN PATIENTS WITHOUT RHEUMATIC DISEASES

Serum from 19/317 non-rheumatic disease patients with positive rheumatoid factors by latex agglutination and with titers comparable to patients with rheumatoid arthritis were assayed for IgM rheumatoid factors by ELISA. Many of these patients (7/19) had liver disease. We characterized the binding specificities of these rheumatoid factors by comparing their binding to heat aggregated human IgG, native human IgG, sheep IgG, and simultaneous binding to sheep and human IgG. Serum from 18/19 patients contained IgM antibodies that bound human heat aggregated IgG when assayed by ELISA, results that were comparable to the latex agglutination test using aggregated IgG. In contrast, there were fewer positive tests using native human IgG (9/19, $\chi^2=8.2$ $p<0.01$), sheep IgG (12/19, $\chi^2=4.8$, $p=0.028$), and human/sheep IgG (2/19, $\chi^2=23.8$, $p<0.001$). Moreover, rheumatoid factors measured by cross-linking of sheep and human IgG produced fewer positive tests than human IgG or sheep IgG alone ($\chi^2=4.6$, p0.032 and $\chi^2=8.3$, $p<0.01$, respectively). The cross-linking assay was positive in one patient with bacterial endocarditis and one patient with liver disease. There was no correlation between the rheumatoid factor ELISA using aggregated IgG and the cross-linking assay ($r=0.39$), showing that the difference in the results between these tests was not due simply to a change in assay sensitivity.

RHEUMATOID FACTORS IN PATIENTS WITH CONNECTIVE TISSUE DISEASES OTHER THAN RHEUMATOID ARTHRITIS

Sera from 14/231 patients with connective tissue diseases other than rheumatoid arthritis with positive rheumatoid factors by latex agglutination and with titers comparable to patients with rheumatoid arthritis were tested for rheumatoid factors by ELISA. Most of the positive rheumatoid factor tests occurred in patients with systemic lupus erythematosus (12/14). In contrast to patients without connective tissue diseases, these rheumatic disease patients produced IgM antibodies that bound equally well to heat aggregated human IgG, native human IgG, and sheep IgG. The ELISA responses to aggregated IgG (18/19 positive) were comparable to the latex agglutination test using aggregated IgG. The rheumatoid factors in these lupus patients could, however, be distinguished from those in patients with rheumatoid arthritis by their inability to simultaneously bind and cross-link sheep IgG and human IgG or their inability to bind autologous IgG that was bound to sheep IgG. For example, the cross-linking assay was positive in fewer lupus patients (3/14) than tests using aggregated IgG (13/14, $\chi^2=11.8$, $p<0.001$), native human IgG (12/14, $\chi^2=9.2$, $p<0.01$), or sheep IgG (11/14, $\chi^2=7.0$, $p<0.01$). These results indicate that many patients without rheumatoid arthritis produce antibodies to sheep IgG, but these antibodies do not bind determinants that cross-react with determinants shared with human IgG.

CORRELATION OF RHEUMATOID FACTORS WITH RHEUMATOID ARTHRITIS DISEASE ACTIVITY

Rheumatoid arthritis disease activity was evaluated in 40 patients and compared to serum rheumatoid factor levels. Patients were chosen who represented a broad spectrum of disease activity. The male predominance reflected, in part, the population of the Veterans Administration. Serum rheumatoid factor titers were assayed in serial dilutions by the latex agglutination test, and these rheumatoid factor titers did not correlate well with rheumatoid disease activity ($r=0.31$). In contrast, the levels of rheumatoid factors measured by ELISA in the cross-linking assay correlated well ($r=0.68$) with rheumatoid disease activity, indicating that rheumatoid factors that cross-link human IgG and sheep IgG occurred primarily in patients with rheumatoid arthritis who had active disease. For example, 0/11 patients with minimal disease activity (activity index <4) were positive compared to 14/16 (87.5%) patients with moderate to severe disease (activity index 6). Positive tests were defined as those greater than 28% of the positive control, corresponding to more than 2 S.D. above the mean for the 548 patients without rheumatoid arthritis. Rheumatoid factors measured by cross-linking of human IgG and sheep IgG also correlated well (r=0.70) with the Westergren erythrocyte sedimentation rate in 23 of these rheumatoid arthritis patients in whom the sedimentation rate was performed. These results further support the association of rheumatoid factors measured by cross-linking of human IgG and sheep IgG with active rheumatoid arthritis.

PRECISION OF THE ASSAY TO RHEUMATOID FACTORS THAT CROSS-LINK HUMAN IgG AND SHEEP IgG

Replicate tests for rheumatoid factor were done using the cross-linking assay to assess the precision of this ELISA method. Intra-batch variation was measured by testing sera with a low, medium, and high response in six replicates each. The tests were performed as a quadruplicate determination on one 96-well plate, and two sets of duplicate determinations each done on separate 96-well plates. The mean ±S.D. (measured as optical density) of six replicates for the high, medium, and low response serum Was 1.56±0.13, 1.38±0.09, and 0.77±0.10, respectively; the coefficient of variation for the 3 groups of serum samples was 0.08, 0.06, and 0.13, respectively. Inter-batch variation was measured by testing a positive sample on five separate occasions. The mean ±S.D. for the five determinations was 1.38±0.14. The coefficient of variation for these inter-batch comparisons was 0.10.

Table 3 summarizes the above comparison of the accuracy of the two assays employed (namely the Agglutination of Latex Particles (Assay A) and ELISA in accordance with the present invention (Assay B)), for detecting the presence of rheumatoid factors.

TABLE 3

| PATIENT GROUP NUMBER | ASSAY A RESULTS (%) | ASSAY B RESULTS (%) |
|---|---|---|
| 1 (RA patients) | 38 - sensitivity | 36.1 - sensitivity |
| 2 (connective tissue patients) | 93.9 - specificity | 98.7 - specificity |
| 3 (non-connective tissue patients) | 94.0 - specificity | 99.4 - specificity |

It is evident from the above results, that the subject assay provides for substantially improved results, in having the same or better sensitivity as the agglutination assay, while having substantially fewer false positives. Furthermore, the positive results appear to relate more accurately with active disease, moderate to severe disease, activity index greater than 6, as compared to minimal disease activity, activity index less than 4. In addition, the subject assay allows for identification of determinants which are common to sheep and human IgG, so as to identify amino acid sequences associated with the binding of rheumatoid factor to immunoglobulins. With the subject assays, one has a much greater assurance that a positive result indicates active rheumatoid arthritis and not other degenerative diseases. Thus, treatments can be directed to the treatment of rheumatoid arthritis, with strong assurance of the existence of the disease.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for detecting the presence of rheumatoid factor in a human host suspected of having rheumatoid arthritis, said method comprising:
   combining a physiological sample from said host with a predetermined amount of a labeled peptide comprising a fragment of rheumatoid factor capable of binding to normal ovine IgG immunoglobulin and normal human IgG immunoglobulin, wherein one of said immunoglobulins is bound to a support in limited amount in relation to the amount of labeled peptide and the other is dispersed in solution, wherein said dispersed immunoglobulin is labeled with a second label; and
   determining the amount of said labeled peptide and said labeled dispersed immunoglobulin bound to said support, as compared to the amount of labeled peptide and labeled dispersed immunoglobulin bound to said support in the absence of sample, wherein the amount of labeled peptide and dispersed labeled immunoglobulin bound to the support is indicative of the presence of human rheumatoid factor in said sample.

2. A method according to claim 1, wherein said labeled peptide comprises 8 to 60 amino acids.

3. A method according to claim 1 wherein said labeled peptide comprises 12 to 30 amino acids.

4. A method according to claim 1, wherein said ovine IgG immunoglobulin comprises sheep immunoglobulin and is bound to said support.

5. The method according to claim 4, wherein said human IgG immunoglobulin is dispersed in said solution and wherein said second label is an enzyme label bound to said human immunoglobulin or a protein to said human immunoglobulin.

6. A method according to claim 5, wherein said human IgG immunoglobulin is bound to said enzyme label via a biotin-avidin or biotin-streptravidin linkase.

7. A method according to claim 5, wherein said enzyme is horseradish peroxidase.

8. A method according to claim 1, wherein said sample is blood diluted at least about 1:100.

9. A method according to claim 1, wherein said labeled peptide is labeled with an enzyme label bound to said peptide or a protein bound to said peptide.

* * * * *